(12) United States Patent
Follonier et al.

(10) Patent No.: US 8,940,523 B2
(45) Date of Patent: Jan. 27, 2015

(54) PIPETTE TIP, PIPETTE SYSTEM AND METHOD FOR PERFORMING ANALYSIS WITH THE PIPETTE TIP AND SYSTEM

(75) Inventors: Stéphane Follonier, Vilters (CH); Linsey Fan, Walnut Creek, CA (US); Pierre Indermuhle, Berkeley, CA (US)

(73) Assignee: CSEM Centre Suisse d'Electronique et de Microtechnique S.A.—Recherche et Developpement, Neuchatel (CH)

( * ) Notice: Subject to any disclaimer, the term of this patent is extended or adjusted under 35 U.S.C. 154(b) by 0 days.

(21) Appl. No.: 13/807,744

(22) PCT Filed: Jun. 30, 2011

(86) PCT No.: PCT/EP2011/061058
§ 371 (c)(1),
(2), (4) Date: Mar. 12, 2013

(87) PCT Pub. No.: WO2012/001127
PCT Pub. Date: Jan. 5, 2012

(65) Prior Publication Data
US 2013/0171673 A1   Jul. 4, 2013

Related U.S. Application Data

(60) Provisional application No. 61/344,332, filed on Jun. 30, 2010.

(51) Int. Cl.
*C12M 1/34*   (2006.01)
*G01N 33/53*   (2006.01)
(Continued)

(52) U.S. Cl.
CPC .......... *G01N 33/5302* (2013.01); *B01L 3/0275* (2013.01); *B01L 3/021* (2013.01); *G01N 33/54306* (2013.01); *B01L 2300/0636* (2013.01); *B01L 2300/0654* (2013.01)
USPC ..... 435/287.1; 422/400; 422/405; 422/82.11; 422/501; 422/524; 435/288.7

(58) Field of Classification Search
None
See application file for complete search history.

(56) References Cited

U.S. PATENT DOCUMENTS

| 6,197,494 B1 | 3/2001 | Oberhardt |
| 2003/0007897 A1* | 1/2003 | Creasey ........................ 422/100 |

(Continued)

FOREIGN PATENT DOCUMENTS

| WO | 2007125407 | 11/2007 |
| WO | 2008036091 | 3/2008 |

(Continued)

OTHER PUBLICATIONS

International Search Report mailed Nov. 23, 2011 for PCT/EP2011/061058, international filing date Jun. 30, 2011.

(Continued)

*Primary Examiner* — Chris L Chin
(74) *Attorney, Agent, or Firm* — Pearne & Gordon LLP (57) ABSTRACT

The present invention relates to a pipette tip (100, 200, 201, 300) comprising a tip body (110) having an inner surface and an outer surface (112). The inner surface (111) defines an inner cavity (120, 320), which has an upper end and a lower end. The upper end has an upper opening (131); and the lower end has a lower opening (141). At least a part of the inner surface (111) is provided with capturing agents (151) of at least one type forming at least one capturing-agent region (150) on the at least one inner surface. The at least one capturing agent region (150) is capable of selectively binding target substances (152) of at least one type comprised in a sample to form at least agent-target conjugates (155), the arrangement of which define at least one agent-target region (156).

20 Claims, 3 Drawing Sheets

(51) Int. Cl.
*B01L 3/02* (2006.01)
*G01N 33/543* (2006.01)

(56) References Cited

U.S. PATENT DOCUMENTS

| | | |
|---|---|---|
| 2003/0119030 A1 | 6/2003 | Zilber |
| 2006/0115384 A1 | 6/2006 | Wohleb |
| 2009/0181463 A1* | 7/2009 | Chen .......................... 436/150 |
| 2010/0072080 A1* | 3/2010 | Karhanek et al. ............ 205/792 |
| 2010/0288058 A1 | 11/2010 | Laiho |

FOREIGN PATENT DOCUMENTS

| | | |
|---|---|---|
| WO | 2009070246 | 6/2009 |
| WO | 2009080874 | 7/2009 |

OTHER PUBLICATIONS

European Office Action dated Oct. 29, 2013 for European Patent Application No. 11743456.3.

Chinese Office Action dated Mar. 25, 2014 for corresponding Chinese Application 201180041897.7.

* cited by examiner

PIPETTE TIP, PIPETTE SYSTEM AND METHOD FOR PERFORMING ANALYSIS WITH THE PIPETTE TIP AND SYSTEM

RELATED APPLICATIONS

The present application is a US National Phase of PCT Application No. PCT/EP2011/061058, filed on Jun. 30, 2011, which claims the benefit under 35 U.S.C. §119(e) of U.S. Provisional Application 61/344,332 filed on Jun. 30, 2010 the disclosure of which is incorporated herein by reference.

FIELD OF THE DISCLOSED INVENTION

The present invention relates to the field of laboratory devices, systems and methods, and more particularly, to the field of pipette devices, systems and methods for performing assays.

BACKGROUND OF THE DISCLOSED INVENTION

A variety of substance handling devices have been proposed assisting in procedures for performing chemical, biological, biochemical, physical analysis and the like, of substances, including the performance of assays such as, for example, Enzyme-Linked Immunosorbent Assay (ELISA). These substance handling devices are usually adapted to securely hold the substance, thereby enabling the transportation of the substance(s) of interest, and may come in the form of a plate that is provided with a binding coating, or which comprises one or more wells, like for example, a capillary channel system or a microtiter plate. As outlined herein below in greater detail, substance handling devices may also be implemented as pipettes.

U.S. Patent Application Publication No. 2003/119030 to Zilber, entitled "Immunoassay Diagnostic Probe and a Method for Use Thereof", discloses a disposable probe for the quantitative detection of specific biomolecules, being the analyte, in a fluid sample, by any known immunoassay procedure which is based on spectroscopic detection. The probe of comprises at least one photodiode chip having a layer of first immunoreactant molecules attached permanently to its surface, said first immunoreactant binds specifically to the analyte, and the photodiode has electronic connectors for transferring the electronic signal generated in the photodiode, upon exposure to light, to a signal processing unit. According to the present invention, part or all of the signal processing components, such as amplifier, A/D converter, etc., can be packaged together with the photodiode in a single semiconductor chip (a photo-sensor chip).

U.S. Pat. No. 6,197,494 to Oberhardt, entitled "Apparatus for Performing Assays on Liquid Samples Accurately, Rapidly and Simply", discloses a device which comprises a channel structure defining a sample well and a reaction volume in communication with each other. The channel structure posses a geometry which causes a liquid sample placed into the sample well to be drawn into and fill the reaction volume via capillary action, wherein after the reaction volume is filled, the liquid sample remains stationary.

Referring now in greater detail to pipettes, the latter are devices used in a laboratory environment for the transport of a measured volume of fluids, for example, from and to vials, troughs and microtiter plates having different numbers of wells (e.g., 96, 384 and 1536) for the analysis of physical, biological, biochemical or chemical reactions. More specifically, the pipette is operative to dispense, and optionally draw, an adjustable amount of fluid from and into a pipette tip, respectively. The volume of fluid that is transportable by pipette tips ranges from microliters to milliliters. Such fluids encompass liquids which may include, for example, samples and reagents.

Pipette tips are commonly made out of polypropylene (PP) and glass. Less common materials are polytetrafluoroethylene, polysulfone, polyethersulfone, polyethylene, fluoropolymers, cellulose acetate, polystyrene, polystyrene/acrylonitrile copolymer, and Polyvinylidene Fluoride (PVDF).

In correspondence with the variety of applications in which pipette tips can be employed, they come in different designs. Accordingly, the length, diameter, and the shape of pipette tips can vary. Pipette tips can for example have a cylindrical or a conical shape. Moreover, different mechanisms are used for drawing and dispensing fluid into and from the pipette tip. These mechanisms include, for example, piston-driven displacement pipettes, positive displacement pipettes and vacuum assisted pipettes. Pipette tips may include external and internal coatings resulting in, for example, conductive, hydrophilic or hydrophobic surfaces by coating the surface. Furthermore, pipette tips may be filled with various compounds such as coated beads, gels such as Thermo Scientific Proxeon. The usage of pipette tips filled with compounds may not be limited to the transport of fluid but also to additional applications such as, for example, filtration and/or purification.

Further developments of pipettes relate to the capability of performing analysis of the level of the fluid in the pipette tip, as outlined herein below.

U.S. Patent Application Publication No. 2010/0288058 to Laiho, entitled "Pipette Body, Pipette Tip and Method" discloses a pipette tip wherein the tip body is provided with a first optical grating structure arranged to conduct light away from the tip body to the side of the inner surface thereof. The tip body is provided with a receiving grating structure arranged to receive the light conducted away from the tip body through the first optical grating structure. A first end of the tip body has means for fastening the pipette tip to the pipette body, and a light-receiving surface optically connected through the tip body to the first optical grating structure. Furthermore, the first end comprises a surface that conducts light away and is optically connected through the tip body to the receiving optical grating structure. Light generating means and means for directing the light to the pipette tip body are arranged in the pipette body.

BRIEF DESCRIPTION OF THE DRAWINGS

The disclosed technique will be further understood and appreciated from the following detailed description taken in conjunction with the drawings in which.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate identical and analogous elements but may not be referenced in the description for all figures.

DESCRIPTION OF THE EMBODIMENTS

It should be understood that an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

It should be understood that the terms "including", "comprising", "consisting" and grammatical variants thereof do not preclude the addition of one or more components, features, steps, integers or groups thereof.

Citation or identification of any reference in the description of some embodiments of the invention shall not be construed as an admission that such reference is available as prior art to the present invention.

The terms "upper", "lower", "right", "left", "bottom", "below", "lowered", "low", "top", "above", "elevated", "high", "vertical" and "horizontal" as well as grammatical variations thereof as used herein do not necessarily indicate that, for example, a "bottom" component is below a "top" component, or that a component that is "below" is indeed "below" another component or that a component that is "above" is indeed "above" another component as such directions, components or both may be flipped, rotated, moved in space, placed in a diagonal orientation or position, placed horizontally or vertically, or similarly modified. Accordingly, it will be appreciated that the terms "bottom", "below", "top" and "above" may be used herein for exemplary purposes only, to illustrate the relative positioning or placement of certain components, to indicate a first and a second component or to do both.

Although some demonstrative embodiments of the invention are not limited in this regard, discussions utilizing terms such as, for example, "processing," "computing," "calculating," "determining," "establishing", "checking", "identifying" or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information storage medium that may store instructions to execute operations and/or processes and/or applications.

It should be noted that the usage of the indefinite articles "a" and "an" when introducing a feature should by no means to be interpreted as there being only one of that feature, unless other specified. Accordingly, the indefinite articles "a" and "an" as used herein encompass the meaning of the phrase "at least one" of the same feature.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

The term "method" refers to manners, means, techniques and procedures for accomplishing a given task including, but is not limited to those manners, means, techniques and procedures either known to, or readily developed from known manners, means, techniques and procedures by practitioners of the art to which the invention belongs.

The descriptions, examples, methods and materials presented in the claims and the specification are not to be construed as limiting but rather as illustrative only.

The term "substance" relates to matter that comprises at least one chemically and/or biologically active substance such as, for example, a chemical compound.

The term "analysis", "performing an analysis" as well as grammatical variations of any of these two terms may refer, for example, to any one of the following procedures: calibration of a detector, measurement and/or monitoring of a biological and/or chemical and/or physical process like, e.g., performing an assay. Correspondingly, the term "analysis" may refer to any procedure employed in, e.g., molecular biology, for testing, measuring, monitoring, initiating, altering, terminating, a process, including, but not limited to processes such as, for example, bioassay, immunoassay (e.g., Enzyme-Linked Immunosorbent Assay (ELISA), Memory Lymphocyte Immunostimulation Assay (MELISA)), a cytotoxicity assay, a DNA assay, an RNA assay, a protein assay, enzyme activity assay, antigen capture assay, stem cell activity assay, a cell counting assay, viability assay, proliferation assay, determining the responsiveness of targets in a substance, reporter assay, migration assays, chemotaxis assay, secretion assay, apoptosis assay, chemosensitivity assay, tetramer assay, gentamicin assay, petrochemistry assay, viral titer assay, radioligand binding assay, or any combination of the aforesaid.

The term "capturing agent" as used herein may refer to, for example, a reagent, which may be, for example, a biological, chemical or biochemical reagent, e.g., as known in the art, for the detection and/or measurement and/or examination and/or production of another substance.

The phrase "investigating a sample for a target substance" as well as grammatical variations thereof, refers to the procedure of determining whether a certain target substance is comprised in the sample, and, if yes, to provide a qualitative (e.g., yes/no) or quantitative assessment of the amount of said target substance in the sample, for example, by employing an assay.

It should be noted that the terms "trapping" and "waveguiding", as well as grammatical variations thereof used herein with respect to the EM waveguiding of light can be interchangeably used in the proper context.

It should be noted that the term "light emanating from an agent-target region" as well as grammatical variations thereof may, for example, refer to the amount of light reflected and/or absorbed (absorbance), fluorescening (by light excitation), and/or chemiluminescing (e.g., by substrate cleavage for light emission) from agent-target conjugates comprised in agent-target regions, or to any other technique, e.g., as known in the art enabling the analysis of agent-target conjugates based on their optical characteristics.

It should be noted that to simplify the discussion that follows, an "agent-target conjugate" may also refer to "a sandwich assay" that may be obtained when applying a sandwich technique.

It should be noted that the terms "tube" and "tube-shaped" as used herein may refer to any elongated body having a cavity, wherein the cross-section of the tube may be at least approximately, cylindrical, oval, polygonal, and/or have any other suitable cross-sectional geometry. Furthermore, the width of a tube-shaped body may be identical, decrease and/ or increase along the longitudinal axis of the tube-shaped body. Accordingly, a tube-shaped may be conical shape for example.

The terms "marker" as used herein may be interchangeably be used with the term "detection reagent".

The terms "washing" and "rinsing" as used herein may be used interchangeably in the proper context.

The geometry of the light propagation path as schematically illustrated in the respective figures should not be construed as limiting.

The term "EM waveguiding medium" may, in the proper context, also refer to a structure or medium defining the boundaries EM waveguiding medium. Accordingly, an EM waveguiding medium may both refer to a waveguiding high-index refraction medium surrounded by a waveguiding low-index refraction medium, the high-index refraction medium having a higher index of refraction than the low-index refraction medium. Moreover, an EM waveguiding medium may also refer to a hollow-pipe waveguide comprising a light-reflecting surface surrounding a dielectric region (e.g., air). The cross-sectional geometry of said structure may be rectangular, elliptical, circular, concave, or any other suitable shape resulting in a light-guiding effect.

SUMMARY OF THE INVENTION

Embodiments of the present invention relate to a pipette tip comprising a tip body having at least one inner surface and an outer surface. The at least one inner surface defines the boundaries of an inner cavity having an upper end and a lower end. The upper end has an upper opening; and the lower end has a lower opening.

According to embodiments of the invention, at least a part of the at least one inner surface is coated with capturing agents of at least one type forming at least one capturing-agent region for target substances on the at least one inner surface. The at least one capturing-agent region is capable of selectively binding target substances of at least one type comprised in a sample to form at least agent-target conjugates defining at least one agent-target region.

According t embodiments of the invention, the pipette tip comprises at least one EM waveguiding medium operative and configured to guide at least some of the light emanating from the at least one capturing-agent region.

According to embodiments of the invention, the at least one EM waveguiding medium is at least one of the following: a side wall, and a cavity of the pipette tip.

According to embodiments of the invention, the at least one EM waveguiding medium comprises at least one medium being, for example, at least one of the following: a medium having a refractive index that is different than the index of refraction of its surrounding medium; a medium surrounded by an inner light-reflecting surface, e.g., to confine the propagation of light in the medium; a medium surrounded by an outer light-reflecting surface, e.g., to shield the medium from ambient light; at least one refracting layer having varying indexes of refraction such that the at least one dielectric layer becomes EM-waveguiding; and photonic-crystal fibers.

According to embodiments of the invention, the pipette tip comprises a light-shield covering at least some portion of the tip body to shield the at least one EM waveguiding medium from external light.

According to embodiments of the invention, at least some part of the pipette tip is retractable (optionally reversibly) into the portion of the tip body that is covered by light-shield, such that the retracted portion is as well shielded by the light-shield.

According to embodiments of the invention, the pipette tip comprising an analysis system.

According to embodiments of the invention, the analysis system comprises at least one sensor; and at least one power source that is operatively coupled with the at least one sensor for powering the least one sensor.

According to embodiments of the invention, the at least one sensor is configured and operative with the pipette tip such to be able to detect light guided in the at least one EM waveguiding medium.

According to embodiments of the invention, the analysis system further comprises at least one controller and at least one storage device that are operatively coupled with the at least one power source.

According to embodiments of the invention, the at least one controller is operative to determine at least one optical characteristic of light detected by the at least one sensor.

According to embodiments of the invention, the analysis system comprises at least one radiation source operative to cause excitation of fluorescence light from the at least one agent-target region.

Embodiments of the invention relate to a method for producing a pipette tip that is operative to perform analysis of at least one substance.

According to embodiments of the invention, the method comprises the procedure of providing (e.g., coating) at least a part of at least one inner surface of at least one side wall of a pipette tip with capturing agents of at least one type to form a at least one capturing-agent region on the at least one inner surface, wherein the at least one inner surface defines the boundaries of at least one inner cavity the pipette tip.

According to embodiments of the invention, the capturing agents are chosen such to selectively bind target substances of at least one type to form agent-target conjugates on the at least one inner surface.

According to embodiments of the invention, the method for producing a pipette tip comprises the procedure of modifying at least one physical property of the pipette tip such that the pipette tip attains a medium having EM waveguiding characteristics.

According to embodiments of the invention, the physical property relates to at least one of the following for example: the index of refraction n; the reflectivity of the inner and/or outer surface of a side wall of the pipette tip.

The present inventions further relates to a method for performing analysis of at least one substance.

According to embodiments of the invention, the method of performing analysis of at least one substance includes the procedure of coating at least a part of at least one inner surface of at least one side wall of a pipette tip with capturing agents of at least one type to form at least one capturing-agent region on the at least one inner surface.

According to embodiments of the invention, the method of performing analysis comprises the procedure of (a) subjecting at least one capturing-agent region to at least one sample for a predetermined period of time such that if the target substance is present in the at least one sample, at least some of the target substance is bound to the capturing agents to form the agent-target conjugates defining at least one agent-target region.

According to embodiments of the invention, the method of performing analysis comprises the procedure of (b) rinsing said inner cavity of said pipette tip to remove unbound sample from the inner cavity; and (c) repeating procedures a) and b) at least once to form a sandwich assay.

According to embodiments of the invention, the method of performing analysis comprises the procedure of modifying at least one physical property of the pipette tip such that the pipette tip attains a medium having EM waveguiding characteristics.

According to embodiments of the invention, the method of performing analysis comprises the procedure of determining at least one optical characteristic of the agent-target region by way of the detection of light emanating from the agent-target conjugates.

According to embodiments of the invention, the method of performing analysis comprises the procedure of determining the at least one optical characteristic of the at least one agent-target region, wherein the procedure of determining the optical characteristic is based on at least one of the following techniques: fluorescence, chemiluminescence and absorbance of said at least one agent-target region.

According to embodiments of the invention, the fluorescence techniques and the absorbance techniques comprise the procedure of irradiating the at least one agent-target region with EM radiation (e.g., light).

DETAILED DESCRIPTION OF THE EMBODIMENTS

It is the object of the present invention to provide a unique pipette tip, system and method for the analysis of substances. More specifically, the pipette tip, system and method are operative to enable analyzing a substance like, e.g., performing an assay, in the pipette tip such that there is no need to dispense the substance from the pipette tip into a diagnostic device such as, for example, a titer plate, for carrying out the analysis. For example, a method according to an embodiment of the invention includes the procedure of performing, in a pipette tip, the step of investigating a sample for a target substance, which includes the procedure of determining whether a certain target substance is comprised in the sample, and, if yes, to provide a quantitative assessment of the amount of said target substance in the sample, for example, by performing assay in the pipette tip.

Figure 1A:
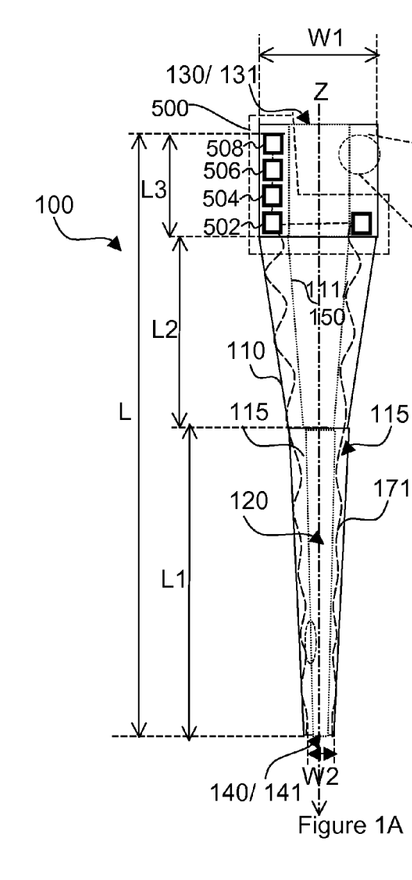
FIG. 1A is a schematic cross-sectional side-view illustration of a pipette tip, constructed and operative in accordance with an embodiment of the invention.
Figure 1B:
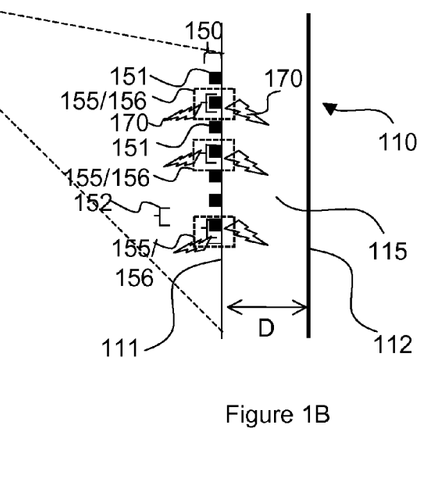
FIG. 1B is a schematic, enlarged, cross-sectional side-view illustration of a part of the tip body forming the pipette tip, wherein the inner side wall of the tip body is coated with an agent capturing region, constructed and operative in accordance with an embodiment of the invention.

Reference is now made to FIG. 1A and to FIG. 1B. According to an embodiment of the invention, a pipette tip 100 comprises a tip body 110 having an inner cavity 120 of longitudinal extent in accordance with the length L of tip body 110. Otherwise stated, tip body 110 is tube-shaped. Tip body 110 further comprises an upper end 130 and a lower end 140 having an upper opening 131 and a lower opening 141, respectively, of inner cavity 120. Inner cavity 120 is adapted to receive and dispense fluids via upper opening 131 and lower opening 141.

Moreover, tip body 110 comprises an EM waveguiding medium extending at least partially longitudinally along circular axis Z of tip body 110, which may constitute an outer side wall 115 of tip body 110, wherein said outer side wall 115 has an inner surface 111 and an outer surface 112, wherein inner surface 111 defines the boundaries of inner cavity 120, which may at least partially of at least approximately conical and/or cylindrical shape. Furthermore, outer side wall 115 of tip body 110 has a minimal thickness D, which is defined by the distance between the inner surface 111 and the outer surface 112 of outer side wall 115.

According to an embodiment of the invention, pipette tip 100 has a converging shape, the width W of pipette tip 100 converging from upper end 130 having width W1, towards lower end 140 having width W2, wherein W1>W2. Correspondingly, pipette tip 100 may have at least partially an at least approximately conical shape.

Inner cavity 120 may be designed such that its volume at least approximately matches the sampling volume required for performing analysis, for example, for depletion assays or to be much smaller than the sampling volume for concentration equilibrium immunoassays. Inner cavity 120 may also be designed to be much smaller than the sampling volume required for performing analysis, the assay being performed by using cycles of suction and dispensing to provide enough volume for analysis.

The surface-to-volume ratio of inner cavity 120 may range, for example, between 1× up to 10× depending on the diameters W1 and W2 but the longest travel distance for a target to reach a capture agent is tens of micrometers (e.g., up to 1000 μm, 900 μm, 800 μm, 700 μm, 600 μm, 500 μm, 400 μm, 300 μm, 200 μm, 100 μm, 90 μm, 80 μm, 70 μm, 60 μm, 50 μm or 40 μm), in comparison to millimeters in 96-well titer plates for example. Accordingly, equilibrium in the analysis, for example, in respect of the concentration of target substances 152 conjugated to capturing agents 151 over a certain diffusion time, is reachable much faster than in comparable systems such as microtiter plate ELISA-based assays. Equilibrium may be attained, for example, within 10, 9, 8, 7, 6, 5, 4, 3, 2 or 1 minute. Due to upper opening 131 and lower opening 141, the probability that bubbles are generated in inner cavity 120 is relatively low, as compared to the probability in systems that have a similar surface-to-volume ratio in a well-format.

According to an embodiment of the invention, upper end 130 of tip body 110 may includes a fastener (not shown) that is operative to detachably couple pipette tip 100 to a pipette handling device (not shown) that may be operative to perform analysis (like e.g., a biochemical assay) in an automatic manner or semi-automatic manner, e.g., as known in the art like, for example, a Pipetman®, a robot, a liquid handling station, or liquid handling robots.

In some embodiments, tip body 110 may include a plurality tip body sections 117 such as, for example, a lower section 117A, a middle section 117B and an upper section 117C. At least some of inner surface 111 of lower section 117A may be devised for being coated with capturing agents 151 of at least one type to form a capturing-agent region 150, which may be a layer. In some embodiments, reagents required for the assay may be preloaded in inner cavity 120 of pipette tip 100 or adsorbed to inner surface 111. In order to preserve molecular activity, said reagents can be encapsulated and/or lyophilized and then preloaded either directly in the inner cavity 120 or adsorbed onto the inner surface 111.

Middle section 117B may be operative to act as a reservoir for substances. Upper section 117C, which comprises the fastener, may as well be operative to act as a reservoir for substances.

Coating of inner surface 111 of tip body 110 may be accomplished by using surface chemistry techniques, e.g., as known in the art like, for example, Silanes forming anchors for capture agent covalent attachment. Coating of the surface may also be designed such to maximize the density of capture agents by using 3-dimensional matrices or polymers, e.g., as known in the art, like for example dextran. A pipette tip according to an embodiment of the invention comprises at least one EM waveguiding medium extending at least partially along the longitudinal axis Z of the pipette tip and which is adapted to confine light to propagate towards, for example, a detector. Such a pipette tip may for example comprise material having a higher index of refraction ($n_{high}$) than the index of refraction ($n_{low}$) (of the matter surrounding said material, wherein the difference in the indices of refraction ($n_{high}-n_{low}=n_{diff}$) is such to effect the properties of an EM waveguiding medium.

Additionally or alternatively, the EM waveguiding layer may comprise a graded refraction layer.

Additionally or alternatively, the EM waveguiding medium of a pipette tip according to an embodiment of the invention may comprise a light-reflecting surface that is shaped such to confine light within a medium surrounded by said light light-reflecting surface.

According to an embodiment of the invention, at least a portion of a side wall (e.g., outer side wall 115) has electromagnetic (EM) waveguiding characteristics that may be made of material that has a higher index of refraction ($n_{high}$) than the index of refraction ($n_{low}$) of the matter surrounding inner surface 111 and outer surface 112 of said portion, wherein the difference in the indices of refraction ($n_{high}-n_{low}=n_{diff}$) is such to result in that said portion of the side wall attains EM waveguiding characteristics. Correspondingly, the index of refraction difference $n_{diff}$ between EM-guiding portion of, e.g., outer side wall 115 and the matter surrounding corresponding portions of inner surface 111 and outer surface 112 may be, for example, at least 0.2, 0.3, 0.4, 0.5, 0.6, 0.7, 0.8, 0.9, 1, 1.1, 1.2, 1.3, 1.4, 1.5, 1.6, 1.7, 1.8, 1.9, or at least 2.

Alternatively, at least a portion of a side wall (e.g., outer side wall 115) may be made of material that has a lower index of refraction ($n_{low}$) than the index of refraction ($n_{high}$) of the inner cavity (e.g., inner cavity 120) so that the inner cavity attains EM waveguiding characteristics. Correspondingly, the index of refraction difference $n_{diff}$ between EM-guiding portion of the cavity and the corresponding portions of the surface between the cavity and the side wall may be, for example, at least 0.2, 0.3, 0.4, 0.5, 0.6, 0.7, 0.8, 0.9, 1, 1.1, 1.2, 1.3, 1.4, 1.5, 1.6, 1.7, 1.8, 1.9, or at least 2.

Additionally or alternatively, at least a portion of a side wall of a pipette tip according to an embodiment of the invention may be coated with an reflective coating (e.g., metal coating) and thereby confining light to propagate within the at least a portion of outer side wall. For example, the surface of side wall 115 may be coated with a reflective metal. Additional or alternative configurations and/or properties may be employed to attain an EM waveguiding medium in a pipette according to an embodiment of the invention.

In some embodiments of the invention, a side wall such as, for example, outer side wall 115, may be configured such to selectively obtain EM waveguiding characteristics. For example, the space between inner surface 111 and outer surface 112 may be hollow and thus be filled with fluid (with an index of refraction of $n_{high}$) such that outer side wall 115 obtains EM waveguiding characteristics. Alternatively, the method may include the procedure of selectively causing inner cavity 120 to attain EM waveguiding characteristics. This may be accomplished by filling inner cavity 120 with a fluid having a higher index of refraction than the side walls surrounding inner cavity 120 such that that latter obtains EM waveguiding characteristics.

To simplify the discussion herein, the examples outlined herein refer to pipette tips wherein at least some of the side walls, and not the cavity or cavities, have EM waveguiding characteristics. However, this should by no means to be construed as limiting. Accordingly, the embodiments outlined herein may be combined at will in connection with the embodiment wherein a cavity, such as, for example, inner cavity 120, has EM waveguiding characteristics.

According to an embodiment of the invention, an analysis system 500 is provided that is operative and coupleable with a pipette tip (e.g., pipette tip 100) in a manner such to be able to analyse processes occurring in the pipette tip. At least some features of analysis system 500 may for example be embeddable in pipette tip 100 and/or a Pipetman® (not shown), e.g., as known in the art. For example, analysis system 500 may be housed, for example, in upper section 117C of pipette tip 100. Pipette tip 100, analysis system 500 and the Pipetman® may be embedded in a longitudinally-shaped housing having, for example, a pen-like shape and dimensions. Correspondingly, pipette tip 100 may for example a height ranging, for example, from 5 to 20 cm, and wherein cavity 120 may for example have a width ranging from 0.5 to 15 mm.

Analysis system 500 may include a sensor 502; a controller 504; a storage device 506; a power source 508; and optionally a radiation source (not shown) operative to cause, for example, the excitation of fluorescence light from agent-target conjugates for example; all of which are operatively coupled with each other. Sensor 502 may be embodied, inter alia, as a light detector operative and configured such to be able to detect at least some of guided light 171 that may be generated, such to convert the detected trapped light 701 into electrical signals (not shown). These electrical signals, which represent the optically detected guided light 171, may be analyzed by controller 504 by executing a set of instructions (not shown) stored in storage device 506 resulting in an application performing the analysis. The analysis may include determining the amplitude (absorption) and/or color of the detected light. Results of said analysis may then be provided to an output (not shown) for interpretation by an operator (not shown) of pipette tip 100.

It should be noted that the arrangement of the features of analysis system 500 as schematically illustrated in FIG. 1A should by no means to be construed as limiting. Accordingly, controller 504 for example may be located outside pipette tip 100. Furthermore, analysis system 500 may additionally or alternatively employ sensors 502 at the bottom end of tip body 110 for the detection of guided light 171 propagating towards said bottom end.

At least some or all elements of analysis system 500 may be disposable. Correspondingly, analysis system 500 may be (fully) disposable or semi-disposable, respectively. When being semi-disposable, at least some elements of analysis system 500 may be disconnectively coupleable with each other. For example, sensor 502, which may be embedded in upper section 117C may be disposed with pipette tip 100 while controller 504, storage device 506 and power source 508 may be disconnectable from sensor 502 and reusable by being re-coupleable with a sensor (not shown) embedded in another pipette tip (not shown).

As is readily apparent from the configuration of pipette tip 100, the latter may be employed as a flow-through cell. Thusly configured, a sample may, for example, be displaced through pipette tip 100, for example, by employing a pump that is operatively coupled to be in communication with upper opening 131 and lower opening 141 of pipette tip 100. Pipette tip 100 may be selectively employed in an open-, closed-, or combined open-closed-loop configuration. In the open-loop configuration, the sample for which the target substance is investigated is always delivered fresh to inner cavity 120, whereas in the closed-loop configuration, the substance comprising the target is re-circulated.

According to an embodiment of the invention, inner cavity 120 may be configured such to selectively produce therein at least approximately laminar or turbulent flow conditions.

Inner cavity 120 of upper section 117C and middle section 117B may be used as a reservoir operative to selectively release, for example, a washing or rinsing solution, thus allowing for selective rinsing with volumes larger than the sampling volume required for performing analysis in one aspiration-dispensing cycle for example. Upper section 117C may optionally also be used for detachably coupling pipette tip 100 to a pipette holder, e.g., as known in the art.

The volume of inner cavity 120 of pipette tip 100, when in operative conjunction with a pipette device (not shown), is selectively adjustable, e.g., as known in the art. The volume of inner cavity 120 may for example be adjustable by employing an air-displacement technique, or a positive-displacement technique. Accordingly, when used as a flow-through cell, the flow-rate of the medium flowing through inner cavity 120 is continuously adjustable by its operator. Additionally or alternatively, the method according to an embodiment of the invention also includes the selection of the cavity volume in accordance with the analysis to be performed. In view of the aforesaid, by employing a pipette device according to an embodiment of the invention like, e.g., pipette tip 100 whose inner surface 111 is coated with capturing-agent region 150 enables the analysis of biochemical reactions in an environment where the liquid volumes in inner cavity 120 are continuously controllable independently from the characteristics of the liquid itself (like, e.g., viscosity). Otherwise stated, the analysis can be performed by employing procedures while obviating the need of relying on capillary effects. The latter type of analysis is herein referred to as "non-capillary analysis".

In accordance with the method of coating inner surface 111 with a capturing-agent region 150, a pipette tip (like, e.g., pipette tip 100) comprising such an capturing-agent region 150 is employable as a disposable flow-through cell for performing an analysis involving the procedure of determining at least one optical characteristic of the agent-target conjugates, as outlined herein below in greater detail.

Additionally or alternatively, pipette tip 100 may be operative such that the flow parameters of fluid (e.g., the substance comprising target) therein is selectively controllable, in a manner e.g., as known in the art. For example, the direction of the flow and/or the velocity of the flow of fluid and/or the flow-rate and/or the dynamic pressure may be controllable, e.g., with respect to at least one other fluid. By controlling for example the velocity or the flow rate of fluid in inner cavity 120, reactions in the latter, which may occur as a part of the analysis being performed, become selectively acceleratable, whereby the probability of molecular diffusion in biochemical reactions may at least be reduced, as compared to a scenario where reactions are not selectively accelerated. Furthermore, control of flow parameters of at least one fluid in pipette tip 100 enables rinsing and washing of inner cavity 120.

Pipette tip 100 may for example be operative such that at least two fluids in inner cavity 120 can be actively mixed with each other, e.g., by shaking pipette tip 100 and/or by displacing fluid(s) into and from inner cavity 120 and/or by causing the fluid(s) to alternantly move up and downward in pipette tip 100 (e.g., by shaking pipette tip 100) and/or provide and draw fluid(s) in an open- or closed-loop configuration into and from inner cavity 120 (by applying pressure), as outlined herein above and/or by controlling the position of particles (e.g., beads) in inner cavity 120 by employing, for example, magnets in operative association with magnetisable beads subjected to corresponding magnetic fields. In some embodiments, capillary effects may be used for the displacement of the substance in inner cavity 120.

Additionally or alternatively, a cavity of a pipette tip like, e.g., pipette tip 100, may be spiral-shaped. Thusly configured, the reaction between capturing-agent and the target may be accelerated.

According to an embodiment of the invention, at least a part of inner surface 111 of tip body 110 may be coated with a sub-layer or a layer of capturing agents (hereinafter: capturing-agent region) 150 of at least one type capable of selectively binding target substances 152 that may be comprised in a sample (not shown) to form agent-target conjugates 155 for which at least one optical characteristic may be determined. Said agent-target conjugates 155 define agent-target regions 156. Capturing-agent region 150 may extend, at least partially, along the longitudinal axis Z of pipette device, and cover at least a certain azimuth with respect axis Z. Correspondingly, capturing-agent region 150 may cover a stripe (not shown), having a certain width, of inner surface 111.

Various techniques may be employed for determining at least one optical characteristic of agent-target conjugates 155 or capturing-agent region(s) 150. These methods are generally based on at least one of the following techniques: fluorescence, chemiluminescence, scattering (e.g., Raman scattering), absorbance and/or any additional or alternative spectroscopic technique, e.g., as known in the art. When employing one of the above-mentioned methods, for example, a detection moiety may be labelled with a marker (not shown), e.g., as known in the art, having for example fluorescening, chemiluminescence and/or absorption characteristics. A fluorescence-based method requires the marker to be irradiated from an external light source for the excitation of the former, i.e., for the fluorescence-based markers to emit light.

Chemiluminiscence-based methods on the other hand may employed without requiring an external light source. More specifically, the detection moiety may be labelled with a chemiluminiscence marker (not shown) such as, for example, an enzyme like (HRP) of alkaline phosphatase (AP). The chemiluminiscent marker may, for example, cleave a substrate (e.g. luminol) emitting chemiluminescent light in the process.

Absorbance-based methods determine the amount of light absorbed by at least one agent-target region, e.g., by determining the amount of light transmitted and/or reflected.

It should be noted that the path of propagation of light 170 as illustrated in the accompanying figures should by no means to be construed as limiting. Accordingly, at least some of light 170 guided in EM guiding outer side wall 115 may follow an at least approximately linear propagation path (not shown).

According to an embodiment of the invention, at least some portion of light 170 emanating from agent-target conjugates 155 may radiate into outer side wall 115 at an angle exceeding the magnitude of the critical angle (not shown) required for total internal reflection (TIR) (hereinafter: guided light 171), resulting in that guided light 171 is trapped and/or guided in outer side wall 115. An example of such a directional emission is the frustrated cone emission.

The confinement of guided light 171 in, for example, outer side wall 115 by, for example, providing an EM waveguiding medium adapted such that most of the emitted light is collected and concentrated to one point, facilitates the detection of light and therefore the accuracy of the analysis of guided light 171, the detected amount of guided light 171 being for example indicative of the concentration of target substances 152 of at least one type relative to capturing-agent region 150.

In some embodiments of the invention, capturing-agent region 150 and/or agent-target conjugate 155 may have EM waveguiding characteristics in association with outer side wall 115 and the matter surrounding capturing-agent region 150 and/or agent-target conjugate 155.

It should be noted that a side wall such as, for example, inner side wall 115, may have various configurations and designs enhancing optical excitation and/or reflectance and/or emission and/or collection of light in a pipette tip. For example, inner side wall 115 may have a non-uniform refraction index like, for example, a gradient index of refraction that decreases towards its outer boundary and which may be designed to at least approximately match the value of the refraction index of the low-index matter surrounding (at least partially) outer side wall 115 to increase the probability of total internal reflection.

According to some embodiments of the invention, at least the waveguiding portions of a side wall of a pipette tip may be made of any EM guiding medium like, for example, dielelecric material (e.g., SiO2, Teflon AF), metals (e.g. Au, Ta2O5, TiO2, Al, Ag) or photonic-crystal fibers.

In some embodiments of the invention, the method may include the procedure of rendering a pipette tip along axis Z waveguiding, e.g., by introducing into the pipette tip an EM waveguiding medium.

Additionally or alternatively, a pipette tip like, e.g., pipette tip 100 may be provided with coatings (not shown) operative to enhance or suppress light 170.

According to some embodiments of the invention, EM waveguiding medium of a pipette tip like, e.g., pipette tip 100, may have a diffractive grating defining at least part of the surface of the EM waveguiding medium, for example, to enhance the coupling efficiency of at least some of the emanating light 170 (like e.g., fluorescence light) into the EM waveguiding medium. More specifically, at least a part of inner surface 111 of outer side wall 115 may have a diffraction grating 116 having period Λ and a grating depth t. To avoid obscuring FIG. 1C, no capturing-agents are illustrated, which may however be present.

Figure 2A:
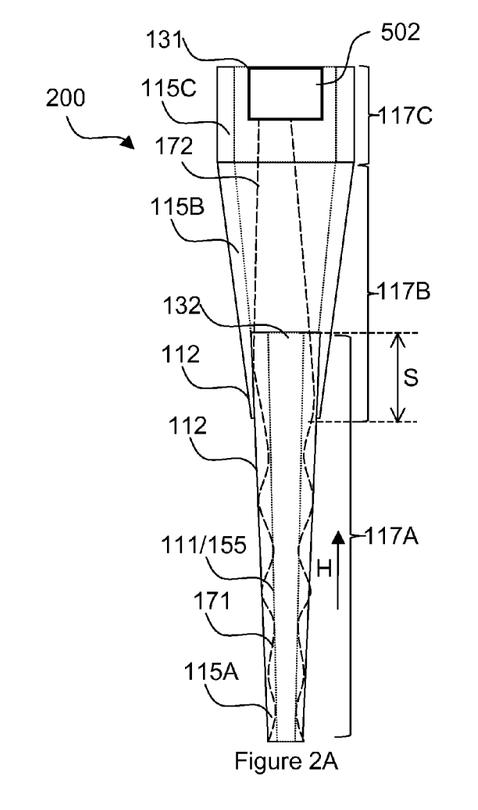
FIG. 2A is a schematic cross-sectional side-view illustration of a pipette tip operative such that light is guided in the lower section of the pipette tip, and then propagates in free space prior to detection, constructed and operative in accordance with another embodiment of the invention.

Further reference is now made to FIG. 2A. According to an embodiment of the invention, a pipette tip 200 may be configured such that at least some of light 170 emanating from agent-target conjugates 155 is first guided as trapped light 171 in an EM waveguiding medium of pipette tip 200, wherein trapped light 171 then exits the EM waveguiding medium (in manner such to further propagate in free space (e.g., cavity 120) of pipette tip 200 in a manner converging to a focal point (not shown). The portion of guided light 171 leaving an EM waveguiding medium to free space is hereinafter referred to as non-trapped light 172.

To enable at least some trapped light 171 to enter free space, at least some of the otherwise aligned structures constituting the EM waveguiding medium may be non-aligned. For example, outer side wall 115 of lower section 117A may be non-aligned with outer side wall 115 of middle section 117B and upper section 117C, as is schematically illustrated with the offsetting distance S between lower section 117A and middle section 117B.

In some embodiments, light propagating in cavity 120 may be detected by detector 502. More specifically, detector 502 may be positioned such to detect at least some of the light propagating in cavity 120, which may constitute free space. Correspondingly, detector 502 may be positioned in alignment with the focal point of the light propagating in cavity 120, i.e., detector 502 may for example be positioned below upper opening 131 in cavity 120 (cf. FIG. 2A) or, for example, above upper opening 131, e.g., in a Pipetman® (not shown).

It should be noted that lower section 117A may constitute as a flow-through cell for fluid flowing from a middle opening 132 of lower section 117A to lower opening 141, and vice versa, from and into upper section 117C, which may act as a reservoir.

Figure 2B:
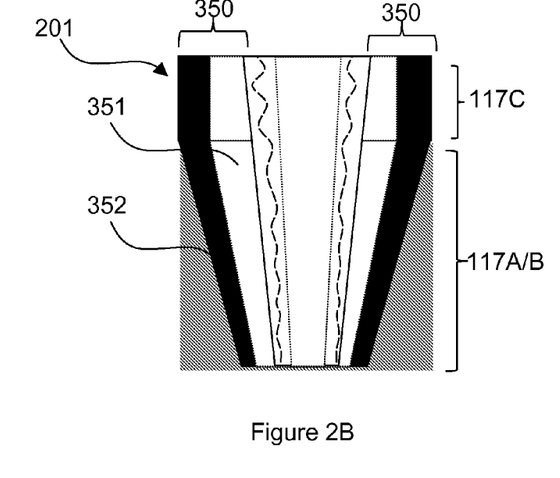
FIG. 2B is a schematic cross-sectional side-view illustration of part of a pipette tip coated with a capturing agent, wherein the lower section of the pipette tip is fully rectracted, constructed and operative in accordance with an embodiment of the invention.

Additional reference is now made to FIG. 2B. A pipette tip 201 according to an embodiment of the invention may be configured such that its body sections 117 are mechanically coupled with each other such that at least two contiguous body sections 117 are longitudinally displaceable (according to arrow H) relative to one another from an extended to a retracted position, and optionally vice versa, i.e., the at least two contiguous body sections 117 may be retractable relative to one another, optionally in a reversible manner.

Correspondingly, the longitudinal extent of the EM waveguiding medium of, e.g., pipette tip 201 like, for example, outer side wall 115 or cavity 120 may be selectively adjustable such to have either the maximal length L1 of lower section 117A, the combined lengths L1 of lower section 117A with length L2 of middle section 117B, or such to maximally extend over the combined lengths L1, L2 and L3 of the three sections 117A, 117B, and 117C, respectively. For example, as is schematically illustrated in FIG. 2B, lower section 117A may be fully retracted in middle section 117B and upper section 117A wherein outer surface 112 of lower section 117A slidably engages with inner surface 111 of middle section 117B. Thusly configured, the EM waveguiding medium may extent over the distance L2 and L3 of middle section 117B and upper section 117C, respectively.

In some embodiments, the total length (L2+L3)>L1 of pipette tip 201 in fully retracted position may for example be such that it is lower than the plate height specifications of a standard microtiter plate reader (not shown). Thusly configured, the pipette tip 201 may be placed in such a reader for measurement. Typical plate heights are 20 to 25 mm and as such, pipette tip 201 may be constructed such as having a total length L of, for example, L2+L3=25 mm. L1=24 mm for example.

According to an embodiment of the invention, a pipette tip such as, for example, pipette tip 201, may include a light shield 350 operative to shield trapped light 171 in lower outer side wall 115 from adverse influence (e.g., interference) of light external to pipette tip 201 for example, by absorption and/or reflection. Additionally or alternatively, 117A can be retracted into the light shield 350 to prevent from adverse influence of light external to pipette tip 117A when retracted. Additionally or alternatively, light shield 350 may comprise a reflective layer operative to reflect light back into EM waveguiding medium. Light shield 350 may include a low-index layer 351 covering, at least partially, outer surface 112 of pipette tip 201 and which has an index of refraction that is lower than the index of refraction of lower outer side wall 115. Thickness t1 of low-index layer 351 may be chosen such that lower outer side wall 115 retains its EM waveguiding characteristics. Moreover, light shield 350 includes a light-absorbing layer 352 covering at least most of the outer surface of low-index layer 351. Light-absorbing layer 352 is operative to absorb most of the light that is external to pipette tip 201 such to reduce possible negative effects (e.g., noise, interference) to guided light 171. For example, light shield 350 may cover, at least partially, only the section of pipette tip 201 embedding sensor 502. Correspondingly, light shield 350 may cover at least a part of upper section 117C only. Additionally or alternatively, light shield 350 may cover at least part of middle section 117B and/or lower section 117A.

Figure 3:
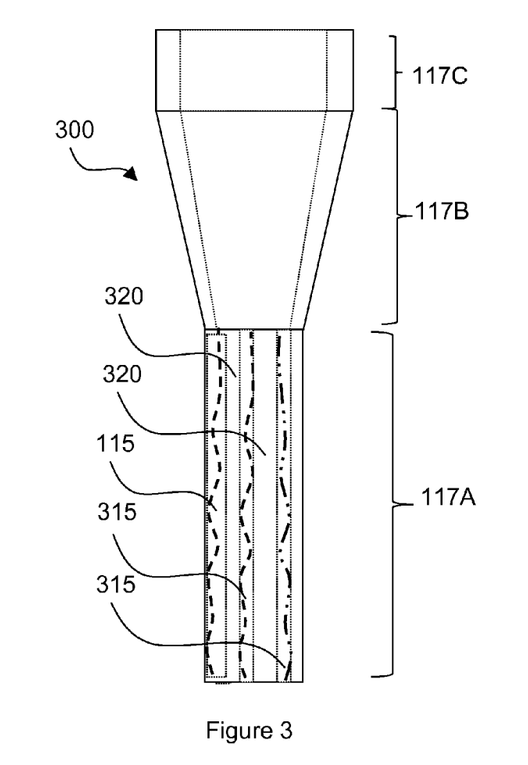
FIG. 3 is a schematic partial cross-sectional side-view illustration of a pipette tip comprising a plurality of cavities, constructed and operative in accordance with an embodiment of the invention.

Further reference is made to FIG. 3. According to an embodiment of the invention, a pipette tip may be operative to perform successively and/or simultaneously analysis related to a plurality of samples for their target substances, respectively. A pipette tip 300 for example may have a plurality of inner cavities 320 having inner surfaces 111. Inner cavities 320 are partitioned by from one another by inner side walls 315.

Outer side wall 115 and inner side wall 315 may be at least approximately concentrically arranged relative to each other.

Inner side walls 315 and outer side wall 115 have a higher index of refraction than inner cavities 320 such that at least some portions of inner side walls 315 and outer side wall 115 exhibit EM waveguiding characteristics, as outlined hereinabove with respect to pipette tip 100 for example. Therefore, inner side walls 315 and outer side wall 115 are operative to trap therein light emanating from, e.g., respective agent-target conjugates, which may be provided at the corresponding inner surfaces of these outer side wall 115 and/or inner side walls 315. Furthermore, each side wall (i.e., inner side walls 315 and outer side wall 115) are operative to guide light at different wavelengths. Thusly configured, in correspondence with the plurality of side walls comprised in pipette tip 300, the latter is operative to be employable for performing a respective number of analyses, successively and/or simultaneously. Performing an analysis, e.g., of biochemical reactions, with respect to different side walls is herein referred to as "multiplex analysis" or "parallel multiplex analysis".

In some embodiments, the pipetting method includes the procedure of performing "mix and match" assays as well as "random access" assays comprising the procedure of assembling different pre-coated pipette tips from multiple racks into a new rack with a different assay configuration.

As is schematically illustrated in FIG. 3, lower section 117A has an at least approximately cylindrical shape. However, this must not be construed as limiting. Accordingly, a lower section of pipette tip 300 may be of at least approximately conical or any other suitable shape. Furthermore, lower section 117A schematically illustrated in FIGS. 1A, 2A, 2B and 3 do not necessarily have to be of at least approximately conical shape, but may be of at least approximately cylindrical or any other suitable shape.

It should be noted that although certain embodiments may only be outlined with respect to a certain pipette tip, this should by no means to be construed as limiting. Therefore, pipette tip 100 and pipette tip 201 may have both a light shield 350 and a plurality of inner cavities 320, for example.

Furthermore, features that are explicitly outlined herein for example with respect to outer side wall 115 only (e.g., index gradient, diffractive grating) may also be employed with respect to inner side walls 315.

In view of the aforesaid, a pipette tip such as, for example, pipette tip 100 (comprising e.g., of SiO2, Teflon AF), and/or metals (e.g. Au, Ta2O5, TiO2, Al, Ag), may be employed for executing a method for performing an analysis such as, for example, immunoassay.

The method may first include the procedure of coating at least a part of an inner surface 111 of a cavity (e.g., inner cavity 120 and/or inner cavities 320) of a pipette tip (e.g., pipette tip 100, 201 or 300) with capturing agents 151.

The method may include the procedure of aspirating the sample containing the target of interest through the cell embodied by, e.g., pipette tip 100, into upper section 117C via upper opening 131.

The procedure may then include the step of incubating capturing agents 151 with the sample in a pipette tip (e.g., pipette tip 100), for example, in a steady state and/or in stop-and-flow state and/or in permanent mixing (continuous push-pull cycles), to enable the target substance, if present in the sample, to conjugate with the agent, resulting in agent-target conjugates 155.

The method may then be followed washing off or rinsing excess sample from the cavity (e.g., inner cavity 120). In some embodiments, the procedure of incubating and the procedure of washing off may be performed a plurality of times.

Furthermore, the method may then include the procedure of introducing the detection reagents into the cavity. In some embodiments, the target substance may already be provided with detection reagents, for example, prior to washing of excess sample from the cavity.

In a next step, the method may include the procedure of determining at least one optical characteristic of the agent-target conjugates by employing, for example, fluorescence, chemiluminescence, or another optical detection method, e.g., as known in the art, to obtain an optically detectable signal.

Finally, the method may include the procedure of interpreting parameters of the optically detected signal such as, for example, absorbance and/or color, for the analysis.

What is claimed is:

1. A pipette tip comprising a tip body, the tip body comprising:
    a lower portion and a middle portion;
    at least one inner surface and an outer surface;
        wherein the at least one inner surface defines the boundaries of an inner cavity;
        wherein the inner cavity has an upper end and a lower end;
        wherein the upper end has an upper opening; and
        wherein the lower end has a lower opening;
    an EM waveguiding medium for receiving light emanating from at least a portion of the at least one inner surface; and
    a light-shield for covering at least the middle portion of the tip body and shielding the EM waveguiding medium from external light;
    wherein the lower portion of the tip body is reversibly retractable into the inner cavity of the middle portion of the tip body covered by the light-shield.

2. The pipette tip according to claim 1 wherein the at least one EM waveguiding medium comprises at least one of a side wall or a cavity of the pipette tip.

3. The pipette tip according to claim 1, wherein the EM waveguiding medium comprises a medium selected from a group consisting of:
    a medium having a refractive index that is different from the index of refraction of its surrounding medium;
    a medium surrounded by an inner light-reflecting surface;
    a medium surrounded by an outer light-reflecting surface;
    at least one refracting layer having varying indexes of refraction to render at least one dielectric layer EM waveguiding; and
    photonic-crystal fibers.

4. The pipette tip according to claim 1, wherein the portion of the at least one inner surface is coated with capturing agents of at least one type forming at least one capturing-agent region on the at least one inner surface;
    wherein the at least one capturing agent region is capable of selectively binding target substances of at least one type comprised in a sample to form at least agent-target conjugates defining at least one agent target region.

5. The pipette tip according to claim 1 comprising a pump that pumps a sample through the upper opening and the lower opening of the pipette tip to form a flow-through cell.

6. The pipette tip according to claim 1, wherein the inner cavity is of a spiral shape.

7. The pipette tip according to claim 1, wherein at least a part of the inner surface has a diffraction grating.

8. A pipette tip comprising a tip body, the tip body comprising:
- at least one inner surface and an outer surface;
- wherein the at least one inner surface defines the boundaries of an inner cavity;
- wherein the inner cavity has an upper end and a lower end;
- wherein the upper end has an upper opening;
- wherein the lower end has a lower opening; and
- wherein a portion of the at least one inner surface is coated with capturing agents of at least one type forming at least one capturing-agent region on the at least one inner surface;
  - wherein the at least one capturing-agent region is capable of selectively binding target substances of at least one type comprised in a sample to form at least agent-target conjugates defining at least one agent target region;
- an EM waveguiding medium for receiving light emanating from the at least one agent target region; and
- an analysis system that comprises:
  - a sensor for detecting light guided in the EM waveguiding medium; and
  - a power source connected with the sensor for powering the sensor.

9. The pipette tip according to claim 8, wherein the analysis system further comprises a controller for determining at least one optical characteristic of light detected by the sensor and a storage device, the controller and the sensor being connected with the power source.

10. The pipette tip according to claim 8, wherein the analysis system comprises a radiation source for causing excitation of fluorescence light from the at least one agent-target region.

11. The pipette tip according to claim 8 comprising a pump that pumps a sample through the upper opening and the lower opening of the pipette tip to form a flow-through cell.

12. The pipette tip according to claim 8, wherein the inner cavity is of a spiral shape.

13. The pipette tip according to claim 8, wherein at least a part of the inner surface has a diffraction grating.

14. A pipette tip comprising a tip body, the tip body comprising:
- at least one inner surface and an outer surface;
- wherein the at least one inner surface defines the boundaries of an inner cavity;
- wherein the inner cavity has an upper end and a lower end;
- wherein the upper end has an upper opening; and
- wherein the lower end has a lower opening;
- an EM waveguiding medium for receiving light emanating from at least a portion of the at least one inner surface; and
- at least a portion of a side wall of the pipette tip having a lower index of refraction than the index of refraction of the inner cavity, such that the inner cavity serves as the EM waveguiding medium.

15. The pipette tip according to claim 14, wherein the portion of the at least one inner surface is coated with capturing agents of at least one type forming at least one capturing-agent region on the at least one inner surface;
- wherein the at least one capturing-agent region is capable of selectively binding target substances of at least one type comprised in a sample to form at least agent-target conjugates defining at least one agent target region.

16. The pipette tip according to claim 14 comprising a pump that pumps a sample through the upper opening and the lower opening of the pipette tip to form a flow-through cell.

17. The pipette tip according to claim 14, wherein the inner cavity is of a spiral shape.

18. The pipette tip according to claim 14, wherein at least a part of the inner surface has a diffraction grating.

19. The pipette tip according to claim 14, wherein a difference in the index of refraction of the side wall and the index of refraction of the inner cavity is at least 0.2.

20. A pipette tip comprising a tip body, the tip body comprising:
- a lower portion and a middle portion;
- at least one inner surface and an outer surface;
  - wherein the at least one inner surface defines the boundaries of an inner cavity;
  - wherein the inner cavity has an upper end and a lower end;
  - wherein the upper end has an upper opening; and
  - wherein the lower end has a lower opening; and
- an EM waveguiding medium for receiving light emanating from at least a portion of the at least one inner surface; and
- wherein the lower portion of-the tip body is reversibly retractable into the inner cavity of the middle portion of the tip body.

* * * * *